United States Patent [19]

Cornelius et al.

[11] Patent Number: 4,880,512

[45] Date of Patent: Nov. 14, 1989

[54] PULSED LIGHT SELECTIVE PHOTOLYSIS PROCESS FOR TREATMENT OF BIOLOGICAL MEDIA AND PRODUCTS MADE THEREBY

[75] Inventors: Paul A. Cornelius; Robin M. Hochstrasser; Neville R. Kallenbach; Harvey Rubin, all of Philadelphia, Pa.; George J. Todaro, Seattle, Wash.

[73] Assignee: Kollmorgen Corporation, Simsbury, Conn.

[21] Appl. No.: 259,508

[22] Filed: Oct. 14, 1988

Related U.S. Application Data

[63] Continuation of Ser. No. 148,113, Jan. 27, 1988, abandoned, which is a continuation of Ser. No. 45,766, Apr. 27, 1987, abandoned, which is a continuation of Ser. No. 690,451, Jan. 14, 1985, abandoned, and a continuation-in-part of Ser. No. 580,848, Feb. 16, 1984, abandoned.

[51] Int. Cl.$^4$ ............................................. B01J 19/08
[52] U.S. Cl. .......................... 204/157.61; 204/157.68; 204/158.21; 530/412; 530/427
[58] Field of Search ....................... 204/157.61, 157.68, 204/158.21; 530/412, 427, 380, 300, 350; 422/24

[56] References Cited

U.S. PATENT DOCUMENTS

| | | | |
|---|---|---|---|
| 3,817,703 | 6/1974 | Atwood | 21/2 |
| 3,876,373 | 4/1975 | Glyptis | 21/54 |
| 3,941,670 | 3/1976 | Pratt, Jr. | 204/158 |
| 3,955,921 | 5/1976 | Tensmeyer | 21/54 |
| 4,021,364 | 5/1977 | Speiser et al. | 252/316 |
| 4,042,325 | 8/1977 | Tensmeyer | 21/54 |
| 4,071,619 | 1/1978 | Peradze et al. | 424/90 |
| 4,265,747 | 5/1981 | Copa et al. | 210/758 |
| 4,395,397 | 7/1983 | Shapiro | 424/101 |

OTHER PUBLICATIONS

Merchant, B., "Injectable Monoclonal Antibody Products: Regulatory Concerns", presented at The Regulatory Affairs Professional Society Meeting on Nov. 9, 1983, Washington, D.C.

"Points to Consider in the Production and Testing of New Drugs and Biologicals Produced by Recombinant DNA Technology", Department of Health and Human Services, Nov. 18, 1983.

Cabrera-Juarez, E. et al., "Oxygen-Independent Inactivation of *Haemophilus Influenzae* Transforming DNA by Monochromatic Radiation: Action Spectrum, Effect of Histidine and Repair", *Photochemistry and Photobiology*, vol. 23, pp. 309-313, (1976).

Borkman, R. F. et al., "The Rates of Photodestruction of Tryptophan Residues in Human and Bovine Ocular Lens Proteins", *Exp. Eye Res.*, 32:747-754, (1981).

Borkman, R. F. et al., "Fluorescence Lifetimes of Chromophores in Intact Human Lenses and Lens Proteins", *Exp. Eye Res.*, 32:313-322, (1980).

Volkert et al., "The Destruction of Tryptophanyl Residues in Trypsin by 280 nm Radiation", *Photochemistry and Photobiology*, vol. 17, pp. 9-16, (1973).

(List continued on next page.)

Primary Examiner—John F. Niebling
Assistant Examiner—Ben C. Hsing
Attorney, Agent, or Firm—Morgan & Finnegan

[57] ABSTRACT

A novel irradiation process and products made thereby. The process treats biological media such as blood fractions, genetically engineered protein products and vaccine preparations. The process photolyzes nucleic acids in preference to proteins in the media, e.g., it inactivates DNA- or RNA-containing pathogens while leaving the proteins substantially intact or functional. In general, the process comprises irradiating the medium with pulsed light of wavelength and flux selected so that (1) the nucleic acids in their ground state absorb radiation and thereby rise to an excited state or states, (2) the nucleic acids in their excited states absorb radiation and thereby rise to higher energy states and undergo photolysis, and (3) the proteins in their ground or their excited states do not absorb sufficient radiation to undergo substantial photolysis. It is surprising and unexpected that nucleic acids in their excited states undergo efficient photolysis whereas proteins under the same conditions in the same medium are kept substantially intact.

55 Claims, 2 Drawing Sheets

OTHER PUBLICATIONS

Hochstrasser, R., "Some Principles Governing the Luminescence of Organic Molecules", *Excited States of Biopolymers*, edited by Robert F. Steiner, Plenum Publishing Corp., (1983), pp. 1–28.

Borkman, R., "Ultraviolet Action Spectrum for Tryptophan Destruction in Aqueous Solution", *Photochemistry and Photobiology*, 26:163–166, (1977).

Fleming et al., "Nonexponential Fluorescence Decay of Aqueous Tryptophan and Two Related Peptides by Picosecond Spectroscopy", *Proc. Natl. Acad. Sci. USA*, 75:(10), 4652–4656, (1978).

Angelov, D. A. et al., "Selective Action on Nucleic Acids Components by Picosecond Light Pulses", *Applied Physics*, vol. 21, pp. 391–395, (1980).

Angelov, D. A. et al., "High-Power UV Ultrashort Laser Action on DNA and Its Components", *Picosecond Phenomena III*, pp. 336–339, (Springer-Verlag), (1980).

Whillans, D., "Optical Detection of the Triplet State of Uracil", *Biochemical and Biophysical Research Communications*, vol. 36, No. 6, pp. 912–918, (1969).

*New England Journal of Medicine*, vol. 310, pp. 69–75, (1984).

Wilson, "Engineering Tomorrows Vaccines", *Biotechnology*, 2(1):29–40, (Jan., 1984).

Antonov et al., "Multiple Photon Processes in Molecules Induced by Picosecond UV Laser Pulses", *Picosecond Phenonomena I*, pp. 310–314.

"Ultrafast Techniques Applied to DNA Studies", *Biological Events Probed by Ultrafast Laser Spectroscopy*, edited by R. R. Alfano, pp. 361–383, (1982).

*Atlas of Protein Sequence and Structure*, vol. 5, Supplement 3, M. O. Dayoff ed, (National Biomedial Research Foundation, 1976).

*Handbook of Biochemistry and Molecular Biology*, 3rd Edition, vol. 2, (Chemical Rubber Co., Cleveland, 1976).

Fleming et al., *Chemistry*, 75:4652, (1978).

D. V. Bent et al., *Journal of the American Chemical Society*, 97:2612, (1975).

A. Anders, "Laser Fluorescence Spectroscopy of Biomolecules: Nucleic Acids", *Optical Engineering*, 22(5):592–595, (1983).

A. Andreoni et al., "Two-Step Photobiology: Application For Lancer Treatment", *Thirteenth International Quantum Electronics Conference*, p. 142.

V. S. Letokhov, "Laser-Induced Chemistry", *Nature*, 305(8):103–108, (1983).

"Two-Quantum Photoprocesses in DNA and RNA Biopolymers Under Powerful Picosecond Laser UV Irradiation," D. N. Nikogosyan et al., *Laser Chem.*, 1984, vol. 4, pp. 297–303.

"Selective Laser Photochemistry of Biomolecules", P. G. Kryukov, pp. 209–224.

"Determination of Parameters of Excited States of DNA and RNA Bases by Laser UV Photolysis", D. N. Nikogosyan et al., *Photochem. Photobiol.*, vol. 35, pp. 627 to 635, 1982.

"This Study of Formation of Single-Strand Breaks in the DNA Chain Under Picosecond Laser UV Irradiation", G. G. Gurzadyan et al., *Photobiochemistry and Photobiophysics*, 4, (1982), 87–93.

"Can Lasers Be Used to Break Chemical Bonds Selectively?", Everett Thiele et al., *Optical Engineering*, vol. 19, No. 1, Jan./Feb., 1980.

"Photofragment Fluorescence Following Ultraviolet Laser Multiphoton Excitation", C. Fotakis, *Optical Engineering*, Sep./Oct., 1983, vol. 22, No. 5.

PULSED LIGHT SELECTIVE PHOTOLYSIS PROCESS FOR TREATMENT OF BIOLOGICAL MEDIA AND PRODUCTS MADE THEREBY

CROSS REFERENCE TO RELATED APPLICATIONS

This is a continuation of copending application Ser. No. 148,113, filed on Jan. 27, 1988, now abandoned, which is a continuation of copending application Ser. No. 045,766 filed on Apr. 27, 1987, now abandoned, which is a continuation of copending application Ser. No. 690,541 filed on Jan. 14, 1985, now abandoned, which is a continuation-in-part application of co-pending application U.S. Ser. No. 580,848, filed in the U.S. Patent and Trademark Office on Feb. 16, 1984, now abandoned.

BACKGROUND

A. Field of the Invention

The present invention relates to the field of the "sterilization" of biological media or fluids such as blood and blood fractions (e.g., blood plasma, blood serum, blood factor VIII, etc ), genetically engineered protein products and vaccine preparations. The term "sterilization," as applied to the present invention, refers to the deliberate alteration, by photolysis, of the chemical structure of nucleic acid entities in the presence of proteins to cause a loss of viability or infectivity of said entities, while substantially maintaining the functionality of those proteins that are also present. An object of this invention is thus to destroy a significant amount or substantially all DNA and RNA based agents, both known and unknown, including infectious nucleic acid molecules capable of transformation, viroids, and viruses or bacteria which are suspected to be in said media, while leaving the proteins in said media to a large degree or substantially completely intact. Until the present invention, it has not been possible to selectively and efficiently photolyze nucleic acids in the presence, and to the substantial exclusion, of proteins. While the process of this invention can be applied to a wide variety of biological media, three illustrative examples are discussed below.

(Blood Sterilization)

Although various techniques have been proposed for sterilizing blood and blood fractions, at the present time such blood and blood fractions are not effectively sterilized prior to transfusion. As a result, a significant percentage of transfusion recipients contract diseases such as hepatitis, and AIDS, from such transfusions. See *New England Journal of Medicine*, Vol. 310, pp. 69–75 (1984).

Techniques which have been suggested, but not widely adopted, include passing blood products through bacterial and/or viral filters, adding antibiotics to such products, etc. These have not proven reliable or efficacious (filters are difficult to maintain with sufficient flow; adding potentially toxic agents is undesirable).

It is current practice to test transfusates to identify those which contain certain pathogens. However, such tests are not 100% accurate and there are many pathogens for which there is no known test, and such tests may be time-consuming and expensive.

(Genetically Engineered Proteinaceous Products of Mammalian Cells)

Most products of recombinant DNA techniques are now produced using altered cells of bacterial strains such as *E. coli*. While certain products, such as the insulin protein, can be quite effectively produced using such non-mammalian strains, certain other protein products are not easily obtained from such strains due to the inability of those strains to produce the desired protein end product in a complex with other desired molecules such as carbohydrates. Indeed, it has been suggested that many of the desirable proteinaceous end products of genetic engineering techniques may not be efficiently or effectively produced using non-mammalian cell strains.

It has been suggested that mammalian cell lines may be well suited to the genetically engineered manufacture of many protein end products. However certain problems are anticipated in the use of such cell lines. See "Injectable Monoclonal Antibody Products: Regulatory Concerns" by Bruce Merchant, presented at the Regulatory Affairs Professional Society Meeting, Nov. 9, 1983; "Points to Consider in the Production and Testing of New Drugs and Biologicals Produced by Recombinant DNA Technology", Department of Health and Human Services, Nov. 18, 1983. Mammalian cells are not generally expected to release or secrete their proteinaceous products directly into their surrounding medium. Accordingly, the harvest of such products will probably require rupturing cellular membranes to release those products into a medium from which they may subsequently be refined or purified. Such rupture, however, will also release mammalian DNA and/or RNA into such medium. Particularly because many easily cultured cell lines are mammalian cancer cells a need exists to ensure that active mammalian DNA or RNA is not present as a contaminant in the proteinaceous end product. This need will remain even if other refining or separation processes are used that do not completely eliminate such DNA or RNA. See "Engineering Tomorrows Vaccines", by T. Wilson, *Biotechnology* 2(1):29–40, January, 1984.

(Vaccine Preparations)

It is also desired to inactivate viral DNA or RNA during the production of "killed" or attenuated virus vaccines. During the production of such vaccines it is often desired to use techniques to weaken the infectivity of such viruses, while retaining some degree of immunogenic integrity in those viruses.

While the exact mechanisms of viral attenuation and immunogenic retentivity are not known, it is theorized that certain attenuating or killing treatments alter the structures of some or all of the protein coats, nucleic acids, or both of the subject virus such that they are incapable of instituting a serious infection, while nonetheless leaving at least portions of the viral coat, and perhaps even the nucleic acid, intact to act as immunogenic site(s) which serve to stimulate antibody production in response to vaccination.

Various techniques are known for killing or attenuating viruses for vaccine use. These include chemical techniques, culturing techniques, etc. Although it has been suggested that some viruses are not tolerant of ultraviolet light, it has also been disclosed that ultraviolet light may be used to inactivate viruses without destroying their immunogenic sites. Compare U.S. Pat. No. 4,021,364 (microencapsulation of virus possible "if ultraviolet light is well tolerated") with U.S. Pat. No. 4,071,619 (purified and concentrated live vaccine is treated with uv radiation at doses of 5,000 to 200,000 erg/cm$^2$ to kill the virus without affecting its immunogenic properties). Despite these general disclosures, a need exists to improve the selectivity of such inactivations such that protein viral coats will better retain their integrities while nucleic acid kill rates are enhanced.

B. Irradiation Of Biological Materials

1. Ultraviolet Light as a Disinfectant.

It is known that ultraviolet light can be used to sterilize certain materials. Typically, such sterilization is effected through prolonged exposure (i.e , minutes to hours) of such materials to conventional ultraviolet light sources in the 50-1000 watt range.

Considerable attention has been given in the past to the effects of ultraviolet radiation on biological systems, particularly with respect to the possible mutagenic, cellular, molecular and/or lethal effects of such radiation on bacterial and viral species. It is known for example, that the DNA of certain species may be inactivated by radiation generally in the 230-470 nm wavelength range, and that the sensitivity of the DNA to such radiation is dependent upon the wavelength of that radiation. These effects have been observed using conventional lamps, such as mercury-xenon or vapor lamps. The capability of steady uv irradiation to destroy DNA is noted in "Oxygen-Independent Inactivation of Haemophilus Influenzae Transforming DNA by Monochromatic Radiation: Action Spectrum, Effect of Histidine and Repair," Cabrera-Juarez et al, *Photochemistry and Photobiology*, 23:309-313 (1976), 2. Molecular Action of Ultraviolet Light.

Scientists are also aware of the behavior of particular organic compounds when irradiated by ultraviolet light. It is known, for example, that different organic compounds exhibit different absorption (extinction) coefficients, that is, the ability of each to absorb energy from light varies from compound to compound as well as with the wavelength of that light. It is further understood that absorbed light may raise a given organic molecule from its ground state to a higher energy state, that the molecule will remain in its higher energy state for a very short period of time (known as the "lifetime" of that energy state), and that that compound may then undergo a chemical reaction leading to the permanent alteration of its structure, or may spontaneously return to the ground state or an intermediate lower energy state. For a general description of the behavior of such organic molecules when irradiated with uv light, see "Some Principles Governing the Luminescence of Organic Molecules", by R. M. Hochstrasser, appearing in *Excited States of Biopolymers*, edited by Robert F. Steiner, Plenum Publishing Corp. (1983).

Proteins and their constituent amino acids have been studied to determine their behavior in response to ultraviolet radiation. Although most of the amino acids of which proteins are comprised do not readily absorb ultraviolet light (of wavelength greater than 220 nm), tryptophan, and to a lesser extent phenylalanine and tyrosine, are known to absorb significant amounts of ultraviolet light, and as a result to be susceptible to structure-altering light-induced chemical reactions, processes herein referred to as "photolysis". It is known, for example, that the photochemical destruction of tryptophan in an aqueous solution may be induced through irradiation at wavelengths between about 240-310 nm, and that the efficiency of that photochemical destruction, expressed in terms of the "quantum yield" for that destruction, attains its maximum value when that compound is irradiated with light in the 240-250 nm range. See "Ultraviolet Action Spectrum for Tryptophan Destruction in Aqueous Solution," by Raymond F. Borkman, *Photochemistry and Photobiology*. 26:163-166 (1977).

Certain aspects of the response of tryptophan to irradiation with ultrashort, picosecond length pulses of ultraviolet light have been the objects of several studies. It is known, for example, that when free tryptophan is excited in aqueous solutions its fluorescence lifetime is dependent upon a number of factors such as pH, temperature, etc., and is generally in the 3 nanosecond range. For tryptophan incorporated in proteins the situation is considerably more complex and remains the subject of much controversy; for instance the fluorescence lifetime drops into the subnanosecond range in hemoproteins (found in red blood cells). See "Non-Exponential Fluorescence Decay of Aqueous Tryptophan and Two Related Peptides by Picosecond Spectroscopy" by G. R. Fleming et al, *Proc. Natl. Acad. Sci. U.S.A.*, 75:(10) 4652-4656 (1978). See also "The Rates of Photodestruction of Tryptophan Residues in Human and Bovine Ocular Lens Proteins, by Borkman et al, *Exp. Eye Res.* 32:747-754 (1981); "Fluorescence Lifetimes of Chromophores in Intact Human Lenses and Lens Proteins," Borkman et al, *Exp. Eye Res.* 32:313-322 at 314 (1980); "The Destruction of Tryptophanyl Residues in Trypsin by 280-nm Radiation," by Volkert et al, *Photochemistry and Photobiology* 17:9-16 (1973).

Even though tryptophan is the least common amino acid of human proteins, the major pathway for uv photodamage (in the 240-310 nm range) to proteins involves tryptophan photolysis since it is the most photolabile amino acids. Thus such radiation may lead to the inactivation of those proteins through photolysis of the tryptophan components, or through photolysis of other aromatic residues. Consequently, while the present invention is concerned with preservation of proteins in general, tryptophan is frequently referred to herein as exemplary.

In "classical" photochemical reactions a single photon causes one molecule to undergo a chemical change However when molecules in any form of matter are irradiated with sufficiently intense light fields, it is known that other photochemical pathways can be opened up as a result of a single molecule absorbing more than one photon. Many examples of chemical change being induced by more than one photon per molecule exist in the scientific literature of the past 30 years. The best known example concerns the photosynthetic process in green plants, which involves the consecutive absorption of red and yellow photons. Another example concerns molecules having metastable triplet states. The long lived triplet states often become populated subsequent to the absorption of a photon by the molecule. This population of triplets may then absorb another photon having either the same or a different color to result in a chemical process. These concepts formed the basis of a recent monograph by V. S. Letokhov (*Nonlinear Laser Chemistry*, Springer-Verlag New York 1983).

Such phenomena have been studied using peptide molecules consisting of a chain of amino acids including tryptophan, alanine and glycine See "Multiple Photon Processes in Molecules Induced by Picosecond UV Laser Pulses," Antonov et al, pp. 310-314 *Picosecond Phenomena I*, Springer Verlag, N.Y 1979 According to this study, when a peptide is irradiated by picosecond pulses the probability of excited molecules absorbing one or more additional photons is much higher than when nanosecond pulses are used.

The nucleic acid components of DNA and RNA and intact DNA have been the subjects of studies in terms of their response to ultrashort high intensity ultraviolet irradiation. These studies have been reviewed by Stanley L. Shapiro in "Ultrafast Techniques Applied to DNA Studies," *Biological Events Probed by Ultrafast Laser Spectroscopy*, edited by R. R. Alfano, pp. 361-383 (Academic Press, New York, 1982). As explained therein, ultrashort light pulses have been proposed to cause the deliberate alteration, or even the destruction, of a complex molecule. Effort has also been directed at achieving selective photochemical reactions in nucleic acids and their components, even though the absorption band of DNA is generally broad, having an absorption peak near 265 nm. See, e.g., Selective Action on Nucleic Acids Components by Picosecond Light Pulses," Angelov et al, *Applied Physics*, 21:391-395 (1980). However, because of the non-specific nature of the absorption band of DNA or RNA materials, and because proteins have a similar broad absorption band, selective and efficient photolysis of DNA in preference to proteins present in the same media has not been achieved prior to the present invention.

It has been reported that DNA and its components, when exposed to high power ultrashort ultraviolet laser action, may successively absorb two uv quanta to thereby acquire energy which exceeds the ionization limit. As a result, some photoproducts are formed which structurally differ from those formed by ordinary "continuous wave" (cw) uv radiation. It has further been suggested that the photo-decomposition efficiency of DNA components under picosecond uv irradiation is more than 10 times higher than under nanosecond irradiation and that the process of two-step excitation of molecules under irradiation depends on many laser radiation parameters such as the radiation wavelength of the first and second steps, the time delay between pulses, the intensity, etc. Thus, it is reported that the process of two-step photo-decomposition may be made more effective for a desired type of nucleic acid base by choosing laser radiation parameters. For example, it has been reported that viruses may be inactivated using uv irradiation intensities from $10^7$ to $10^9$ watts per square centimeter to cause single-strand breaks in the DNA, whereas the use of lower power uv irradiation is reported to result in inactivation because of the formation of pyrimidine dimers of the cyclobutane type. See "High-Power UV Ultrashort Laser Action on DNA and its Components," Angelov et al, in *Picosecond Phenomena III*. edited by Hochstrasser et al pp. 336-339 (Springer-Verlag, New York, 1980).

It has further been reported that multi-step, multiple photon excitation of atoms and molecules by laser radiation provides a basis for non-linear laser photochemistry. See Antonov et al, *Picosecond Phenomena I*, Springer-Verlag, N.Y. (1979), and "Optical Detection of the Triplet State of Uracil", D. H. Whillans et al, *Biochemical and Biophysical Research Communications*, 36(b): 912-918 (1969).

3. Further Background Regarding Quantum Mechanics of Nucleic Acids and Proteins.

The interaction between light from a conventional source and a sample of molecules can be understood by means of a few simple physical principles. A source producing light energy at a single wavelength may be described in terms of that wavelength and its intensity as expressed in energy per unit of illuminated area per unit of time. In quantum mechanical terms, light energy may be described using the Planck relationship $E = hv$, where E is the energy of one photon, h is Planck's constant, and v is the frequency of the light. In this terminology, the light intensity may be expressed in units of photons per square centimeter per second, or photons $cm^{-2} sec^{-1}$.

The concentration of sample molecules in a target region may be expressed in terms of the number of moles per liter (molarity M). As the light passes through the sample it is absorbed at least in part by the molecules, the efficiency of that absorption being a characteristic of the particular molecule and varying according to the wavelength of the light used. The extinction coefficient, e, is a measure of the absorption efficiency and has the units $M^{-1} cm^{-1}$. A graph of the extinction coefficient versus wavelength of light is the absorption spectrum of the molecule.

Quantum mechanically, the absorption of a photon by a molecule is accompanied by a transition, or change in the quantum state of the molecule. In a typical case, all of the molecules may be assumed to occupy their lowest energy ("ground") quantum state before the light source is switched on. In the presence of light, some of the molecules undergo transitions from the ground state to a higher energy ("excited") state. A molecule cannot remain in such a state indefinitely and must inevitably lose its excess energy in some way. The fate of any single molecule cannot be known in advance but only expressed in terms of quantum mechanical probabilities or quantum yields (Q). An important parameter associated with each excited state is the lifetime (T), which is the average amount of time that an undisturbed molecule occupying that state remains in that state.

There are several possible consequences of exciting a molecule with light. The molecule may spontaneously return to the ground state, either directly or by first entering an intermediate state. It might alternatively absorb another photon to reach an even higher energy state. Another possibility is that the molecule will undergo photochemistry and thus suffer an alteration in its chemical structure; in many cases the alteration is permanent and the molecule cannot return to its original ground state. When such photolysis is used to cause a chemical change in a DNA or protein molecule, the biological functioning of the molecule may be impaired or destroyed.

Absorption coefficients, excited state lifetimes, and quantum yields are intrinsic molecular characteristics and, as discussed above, have been determined through experimentation for many molecules. From a knowledge of these values and the parameters of the light source one can calculate the rate of a photochemical reaction.

The present invention is concerned with irradiation of a media which comprises nucleic acids, e.g., in the form of DNA molecules, and proteins. The following calculation demonstrates that the consequence of irradiating the media with a conventional source of ultraviolet (uv) light, such as discharge lamp, is the destruction of the proteins as well as the DNA, since both chemicals absorb the light and are destroyed by the subsequent photolysis. The calculations below are based upon the Beer-Lambert absorption law, which defines the radiative transition rate per molecule (r) as the product of the absorption cross-section and the light intensity $$r = I \times s$$

where I is the light intensity in photons cm$^{-2}$sec$^{-1}$ and s is the absorption cross-section in cm$^2$. The absorption cross-section (s) is obtained from the extinction coefficient by the formula s=3.82×10$^{-21}$×e, where the extinction coefficient is in units of M$^{-1}$ cm$^{-1}$. s has the units of cm$^2$. The overall rate per molecule (R) of the photochemical reaction is the product of the transition rate and the photochemical quantum yield.

$$R = I \times s \times Q$$

From a knowledge of R one can compute the probability, (P), that a given molecule will remain unreacted during a time interval of t seconds:

$$P = 10^{-(R \times t)/2.303}$$

In this calculation, the attenuation of the light beam as it passes through the sample medium is neglected. This approximation is valid assuming that the subject sample meets the thin layer criterion discussed herein, that is, that the sample is sufficiently thin or the absorption coefficient sufficiently small so that the attenuation of the light beam through the sample medium will be small.

Human blood plasma, for example, contains a number of different protein molecules. Most amino acids (the individual units from which proteins are constructed) do not significantly absorb near-uv or mid-uv light and are not affected by the presence of such light. Tryptophan, discussed above, is a notable exception. A typical plasma protein contains only a few (0-15) tryptophans, but even a small number is sufficient to make a protein susceptible to photochemical damage. See *Atlas of Protein Sequence and Structure*, Vol. 5, Supplement 3, M, O. Dayhoff ed. (National Biomedical Research Foundation, Silver Spring, Md., 1976). As discussed above, the extinction coefficient and photochemical quantum yield have been measured for tryptophan, thus making it possible to estimate the rate at which a given light source will damage a given protein. See the *Handbook of Biochemistry and Molecular Biology*, 3rd edition, Vol 2 (Chemical Rubber Co., Cleveland 1976); G. R. Fleming et al, *Chemistry* 75:4652 (1978) and references cited therein; and Raymond F. Borkman, *Photochemistry and Photobiology*, 26:163 (1977) supra.

If blood plasma is taken from a donor with a viral infection, the plasma may contain as many as 1 million viruses per cubic centimeter. A virus consists of one or more DNA (or RNA) molecules inside a coat, typically a protein or protein-lipid complex. Other infectious agents called viroids, which consist only of an RNA molecule, are also known. The viral coat is relatively transparent to uv light, but the nucleotide bases of DNA (or RNA) are all strong absorbers. A sufficient dose of uv light will create photochemical lesions in the viral DNA, resulting in an irreversible loss of infectivity. Many experiments have measured the rate at which uv light deactivates viruses under various conditions. These experimental data effectively define a quantum yield for viral inactivation, permitting a comparison between the efficiency of viral inactivation and the efficiency of protein damage for a given light source. See *Photochemistry and Photobiology*, 26:163 (1977) supra.

TABLE I.

| Extinction coefficients and absorption cross-sections at a wavelength of 266 nm | | |
|---|---|---|
| Species | e(M$^{-1}$cm$^{-1}$) | s(10$^{-17}$cm$^2$) |
| Tryptophan | 4,000 | 1.5 |
| Nucleic acid (average) | 10,000 | 3.8 |
| Viral DNA molecule | 1 × 10$^9$ | 3.8 × 10$^5$ |
| Model plasma protein | 40,000 | 15.0 |

Notes: The above figures assume a protein having 10 tryptophans and a viral DNA molecule containing 50,000 nucleic acid base pairs. There are four different bases in DNA and the above extinction coefficient represents an approximate average (the four bases have very similar absorption spectra). Some viruses contain RNA instead of DNA; the spectral properties of the two polymers are similar. There are two other amino acids (tyrosine and phenylalanine) that have significant uv absorption. Their extinction coefficient 266 nm are 700 and 100 respectively.
Concentration of viruses in an infected human ... ca. 10$^6$/ml.
Concentration of proteins in human plasma ... ca. 10$^{-3}$ M.
Radiation flux (the product of the light intensity and the irradiation time, i.e., I × t.) at 254 nm necessary to reduce viral DNA activity by 90% ... 1.3 × 10$^{17}$ photons/cm$^2$.
Equivalent "quantum yield" for viral destruction ... 2 × 10$^{-6}$.

Table I presents the quantum yield and cross-sections of both a model virus and a model tryptophan-containing protein in the near uv part of the spectrum In addition, since a unit (450 ml) of infected blood may contain as many as 4.5×10$^8$ viruses, sterilization should preferably reduce the viral activity by a factor of approximately at least 10$^8$. In other words, the probability of an individual virus remaining unreacted (P) should be less than 10$^{-8}$. From these data it has been calculated that a continuous wave light source operating near 260 nm would be required to supply a total radiation flux of 2×10$^{18}$ photons per cm$^2$ in order to achieve the desired condition (a probability of unreacted viruses of less than 10$^{-8}$) of viral deactivation. It follows that this amount of radiation will also result in massive protein destruction (P=10$^{-11}$ for the model protein of Table 1). Thus, such a light source is not capable of sterilizing such biological fluids in a useful way.

It should also be noted that the Beer-Lambert law does not always provide a correct description of the rate of a photochemical process, since it can only be applied in cases where the intensity of the light source is kept relatively low. Modern pulsed lasers are capable of producing picosecond (10$^{-12}$ sec.) bursts of extremely high intensity. A single pulse from such a laser can attain a power in excess of 1 gigawatt (10$^9$ watts), while continuous wave lasers or "classical" sources (such as discharge lamps) typically operate in a range of 10 to 1000 watts. The effects of such intense pulses on the molecules of the sample can be understood by comparing the differences between the processes of FIGS. 1 and 2. When the intensity of incident photons is relatively low, there is only a small probability that a molecule will absorb a second photon while in an excited state. Thus, as seen in FIG. 1, there is a high probability that after a single photon has raised the energy level from ground state A to excited state B, the molecule will spontaneously undergo photolysis, form a lower energy state and/or return to the ground state without absorbing another photon. In a picosecond pulse, on the other hand, the photon intensity is quite high. In this case there is a significant probability that a second photon can be absorbed while the molecule is still excited, and that in this way the molecule can reach energy levels that are inaccessible by simple one-photon Beer-Lambert type processes.

Other workers have recently applied some of the quantum mechanical concepts discussed above to inactivation of free nucleotides. See A. Andreoni et al "Two-Step Laser Photobiology Application For Cancer Treatment", *Thirteenth International Quantum Electronics Conference*, pp. 142; A. Anders "Laser Fluorescence Spectroscopy of Biomolecules: Nucleic Acids, *Optical Engineering*, 22(5), 592-595 (1983). None, however, has accomplished the photolysis of DNA or RNA nucleic acids in preference to and in the presence of proteins, i.e., an efficient sterilization process, as provided by the present invention.

The achievement and advantages of the present invention can be further appreciated by reference to U.S. Pat. Nos. 4,395,397, 3,837,373, 3,941,670, 3,817,703, 3,955,921, 4,042,325 and 4,265,747, none of which teaches a selective and efficient photolysis of nucleic acids in biological media while leaving proteins and other biological materials in the media undisturbed. U.S. Pat. No. 4,395,397, in particular, is illustrative. There, it was desired to kill unwanted cells, e.g., cancer cells, in a suspension of living cells. A process was disclosed whereby the cancer cells were first identified or "tagged" by means of fluorescent antibodies and the cells so tagged were then killed, one cell at a time, with laser light. In contrast, and as will be apparent from the description below, the present invention does not require identification of the unwanted nucleic acids prior to treatment of the biological medium desired to be sterilized Indeed, the process of the e.g., blood, without first determining whether or which nucleic acid-based pathogens, e.g., cancer cells or viruses, are present. Moreover, the present invention does not require use of a "tag" and does not require response to a fluorescent or other "signal".

SUMMARY OF THE INVENTION

The present invention provides a process for treating a biological medium to enhance photolysis of nucleic acids relative to proteins present therein. The invention also provides products made by said process. The process comprises irradiating the medium with pulsed light of wavelength and flux selected so that (1) the nucleic acids in their ground state absorb radiation and thereby rise to an excited state or states, (2) the nucleic acids in their excited states absorb radiation and thereby rise to higher energy states and undergo photolysis, and (3) the proteins in their ground or their excited states do not absorb sufficient radiation to undergo substantial photolysis. By application of the process, the medium is sterilized, e.g., nucleic acid or viral activity is reduced by at least $10^4$ while protein functionality is reduced by no more than 40%. Such results have not been achieved prior to the present invention and it is surprising and unexpected that nucleic acids in their excited states can be made to undergo efficient photolysis while proteins under the same conditions in the same medium can be kept substantially intact. Preferably, the biological medium is a solution selected from blood, blood fractions, genetically engineered proteinaceous products of mammalian cells, and vaccine preparations containing viral DNA or RNA in a protein coat. All of these media share the common characteristic of containing nucleic acids (e.g., in the form of DNA or RNA) and proteins.

Thus, in accordance with certain embodiments of the present invention, a solution of proteins, e g , tryptophan-containing proteins, and nucleic acids is treated to selectively photolyze or inactivate those nuclei acids. These embodiments comprise irradiating that solution with a first light pulse of a first wavelength and of sufficient flux to raise a portion of those nucleic acids from their ground state to one of their excited states, and of further irradiating those nucleic acids in those excited states with a second light pulse which is preferentially absorbed by nucleic acids in those excited states to raise said nucleic acids to even higher energy states from which the spontaneous photolysis of said nucleic acids occurs In performing these embodiments, the flux and wavelengths of the first and second light pulses are carefully selected to minimize the photolysis of the amino acids, such as tryptophan, of said proteins. This can be accomplished, for example, by the selection of pulses that are of substantially the same wavelength and flux, or by the selection of pulses that are of substantially the same wavelength and different flux, or, by the selection of pulses that are of different wavelength and flux. The pulses can be repeated and/or sequenced, if desired, in various ways as explained in more detail below In general terms, therefore, the present invention relates to the use of a sequence of light pulses suitably arranged by time and wavelength in order to control the outcome of a photolysis, e.g., to selectively react DNA or RNA molecules in the presence of proteins.

Accordingly, it is an object of this invention to provide an irradiation process for sterilizing biological media. It is another object to provide an irradiation process for sterilizing a biological medium selected from blood, blood fractions, genetically engineered proteinaceous products of mammalian cells, and vaccine preparations. It is another object of the invention to provide a novel irradiation process for treating biological media to photolyze nucleic acids in preference to proteins present therein. It is another object of this invention to provide a process which utilizes a sequence of light pulses suitably arranged by time, wavelength and intensity to control the outcome of a photolysis, e.g., to enhance the difference in the relative rates of photolysis as between nucleic acids and proteins. It is another object of the invention to provide treated biological media, e.g., media in which the nucleic acids have been photolyzed in preference to proteins present therein. It is another object of the invention to produce, by the process of the invention, nucleic acid inactive, protein-rich end products, e.g., sterilized proteinaceous end products of mammalian cell origin, killed virus vaccines, blood and blood fractions.

DESCRIPTION OF THE PREFERRED EMBODIMENTS

Figure 1:
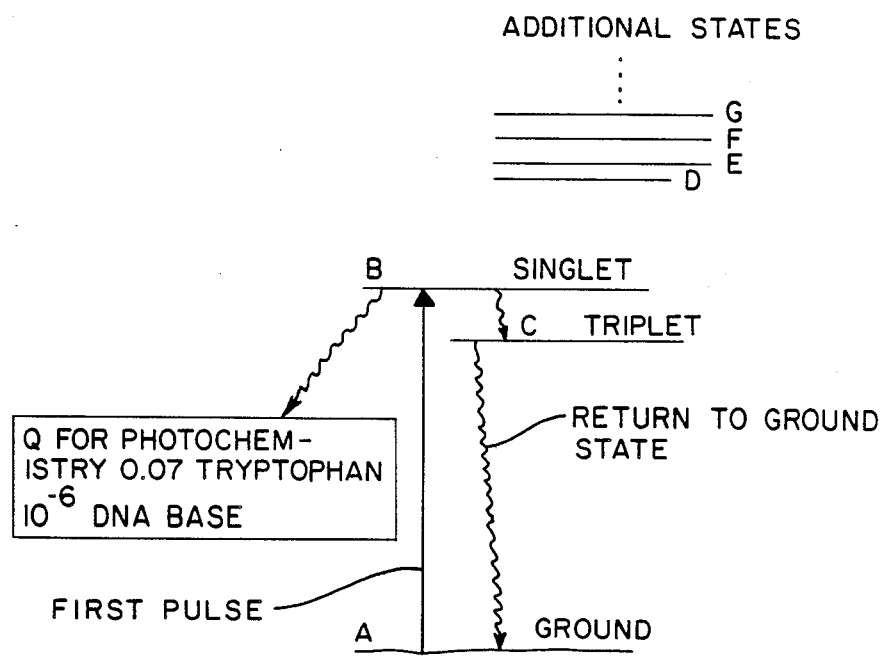
FIG. 1 is a diagram illustrating certain energy states of DNA and tryptophan as well as certain photochemical processes that result from irradiating these compounds with a classical light source which predominantly results in single photon photochemistry.

A preferred embodiment of the present invention involves flowing a thin layer of the biological medium, in the form of a fluid, through a target region which is disposed to receive the output pulses of a light source, e.g., a laser. As used herein, the term "thin layer" refers to a layer of fluid which transmits more than 10% of the light energy which is incident thereon. Depending on the nature of the medium and its possible dilution, layers satisfying this criteria are expected typically to have thicknesses of from 0.1 mm to several mm., preferably thicknesses on the order of less than 0.5 mm, and preferably about 0.2 mm. The actual flow rate of the fluid through the target region depends upon the effective area of the incident laser beams and the intensities and repetition rates of the pulses, as described hereinafter. It is anticipated that in most installations the flow across each millimeter of target region width can be established at about 5 milliliters per second through a quartz channel which defines a layer of generally square or rectangular cross-section and which presents as part of its largest surface an area equal in width to or slightly narrower than the width of the incident light beam.

The pulsed light used in this invention is preferably comprised of laser pulses. Pulsed laser systems produce their output pulses in a repetitive fashion. The rate at which the pulses are produced is dependent on the laser hardware and is called the "repetition rate." In the treatment of the biological medium the pulses are preferably directed onto a small spot (either circular or of some other shape) referred to as the "target region." This region will, in most instances, be too small to contain the entire sample to be processed. In these instances the sample can be flowed through the target region until the entire sample has been irradiated. Alternatively, the laser beam can be caused to scan over the area of the sample and/or the sample can be processed as a sequence of sub-samples. To insure that each volume element of the sample is subjected to substantially the same irradiation conditions, each volume element should receive repetitions of the same cycle of laser pulses.

In a specific embodiment of the present invention, blood plasma or blood serum can be sterilized in the presence of intact blood cells. A red blood cell contains no DNA and is relatively resistant to radiation at the wavelengths and fluxes described herein. However, a single red blood cell has sufficient optical density to absorb the bulk of the incident radiation, thereby shielding the portion located behind said blood cell. Accordingly, when whole blood is to be processed it is preferred to establish a thin channel flow of blood through the target region such that the cells will pass "single file" through that region. The plasma or serum surrounding these cells is then irradiated from opposing directions to ensure that the entirety of the subject plasma will receive the desired amounts of uv radiation.

The quantum yield of a two-photon photochemical process as is involved in the present invention depends upon the intensity of the incident light For a typical laser system, the energy content and the time duration of the output pulse are initially determined by the laser hardware The intensity of the laser light at the target region can be brought to virtually any desired value, however, by passing the laser pulse through a lens (or set of lenses) to control the cross-sectional area of the pulse as it enters the target region For this reason a wide variety of existing laser systems can be used to practice the present invention, and the choice of a particular laser is largely dictated by cost, reliability, and the processing rate desired.

Pulsed lasers are currently available with repetition rates ranging from 0.01 Hz (pulses per second) to $10^8$ Hz. Those lasers having high repetition rates typically produce pulses that are weak; such pulses should be focussed to a very small spot to generate sufficient intensity to carry out the present process. Lasers with very low repetition rates typically produce pulses of enormous energy, but presently suffer from poor reliability. To provide both adequate peak power (e g., to stimulate the two-photon absorption process described herein) and adequate average power (e.g., to treat sufficient volume of material), a preferred laser for the present invention (A) has a repetition rate between 10 Hz and 1,000,000 Hz, more preferably between 10 and 10,000 Hz and most preferably between 100 and 10,000 Hz and (B) is capable of producing pulses of durations less than about $2 \times 10^{-8}$ seconds, and preferably $10^{-10}$ to $10^{-12}$ seconds while emitting light of extremely high intensity. This laser may be a conventional laser, such as a YAG laser (and its associated optical components), which is capable of providing the wavelength(s), intensities, and pulse frequencies described herein.

Pulsed lasers typically operate at a single fixed wavelength. Numerous methods are known in the art for generating additional wavelengths from this original pulse, including harmonic generation, synchronous dye laser operation, and optical parametric oscillation. In those embodiments of the invention which use pulses of different wavelength, those pulses can be derived from a single original pulse using one of the methods known to the prior art.

Considerations of target region size, sample processing rate, and laser repetition rate apply equally to all of the embodiments of the invention described herein. While the embodiments are described in terms of pulse duration and flux, those skilled in the art can relate these variables to intensity, and to target sizes and sample processing rates by the choice of particular laser systems.

The present invention recognizes the importance of maintaining the integrity of blood plasma or serum proteins, while performing DNA or RNA inactivation. Even though blood serum proteins are also susceptible to non-linear inactivation, the present invention recognizes that such proteins can be preserved substantially intact by carefully selecting the wavelengths and intensities of the first and second pulses to favor the photolysis of nucleic acids. For example, this process can increase the efficiency of tryptophan photolysis by a factor calculated to be only about 3 or below while simultaneously increasing the efficiency of DNA photolysis by a factor of about 5,000. It should be understood that the enhancement of the difference in the relative rates of photolysis as between nucleic acids and proteins achieved by the process of this invention is of paramount importance and that the numbers "3" and "5,000" are calculated for the purpose of illustration and may not be applicable in every case.

Figure 2:
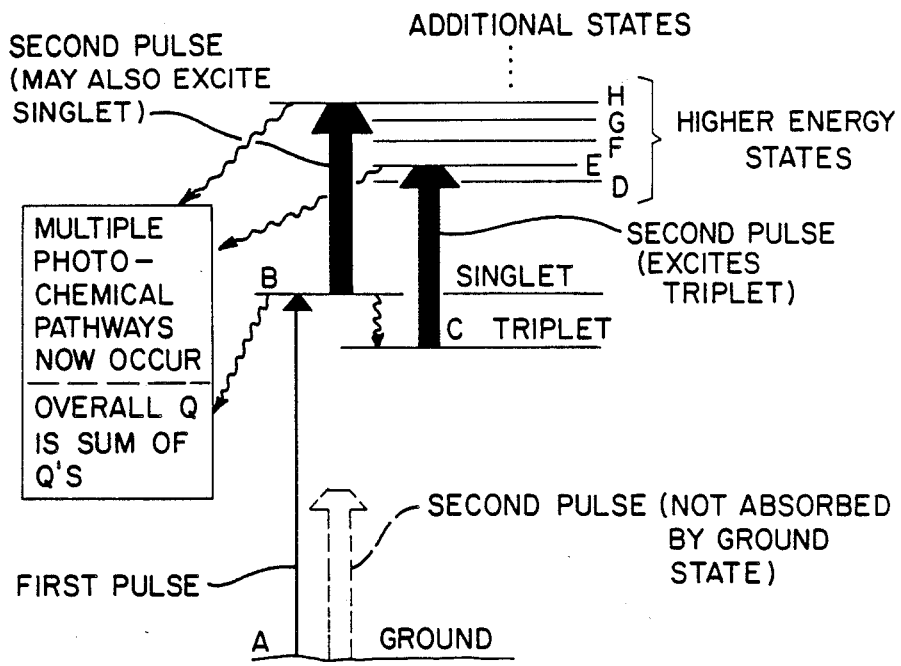
FIG. 2 is a diagram similar to FIG. 1 illustrating the additional photochemical processes of tryptophan and DNA induced by a preferred ultrashort two-pulse differential wavelength laser irradiation process of the present invention.

As an example of the process of the present invention, using a pulsed laser, it is now possible to conduct a two-pulse photolysis, as shown schematically in FIG. 2. The first pulse is chosen to have a relatively low intensity so as to excite a fraction of the molecules to state B by a simple Beer-Lambert process. Of these excited molecules, approximately 13% in the case of tryptophan and 1% in the case of a nucleic acid, will reach state C through the occurrence of intrinsic molecular processes. A second pulse of light of extremely high intensity is now used to cause further absorption events to take place. The existence of higher energy states such as D, E and F has also been demonstrated experimentally and these states are expected to provide a high probability of photochemical reaction. See D. H. Whillans et al., supra, and D. V. Bent et al, *Journal of the American Chemical Society* 97:2612 (1975). It is important to note that the ground state A cannot absorb photons efficiently from the second pulse, since there is no quantum state available of the appropriate energy The consequence of this two pulse irradiation process is that virtually every molecule that reaches the triplet state C will be forced to react photochemically under the influence of the second pulse. The overall rate of the photochemical reaction depends, in this case, on the rate of producing triplets; this will increase the efficiency of tryptophan photolysis by a factor of 3 but will simultaneously increase the efficiency of DNA photolysis by a factor of 5,000. The effect of the two pulse scheme is illustrated in FIG. 2. In this example, the sterilization condition (P less than $10^{-8}$) can now be achieved using a 260 nm flux of only $4.6 \times 10^{14}$ photons per cm$^2$. This flux will yield a P value for the proteins of 0.99; i.e., about 99% of the protein functionality of the material will be retained.

The present invention thus provides, in one embodiment, novel processes for sterilizing biological fluids such as human blood and blood fractions, which processes involve the use of intense pulses of laser light to destroy infectious agents while maintaining high functional levels of proteins and other vital components.

In an illustrative general embodiment, the invention provides a process for treating a solution of proteins and nucleic acids such as DNA or RNA to selectively inactivate said nucleic acids, comprising: (a) irradiating said solution with a first light pulse of a first wavelength of sufficient flux to raise a portion of said nucleic acids from their ground state to an excited state yet not sufficient to inactivate the proteins in said solution; and (b) irradiating said nucleic acids while in said excited state with a second light pulse which is preferentially absorbed by nucleic acids in said excited state but not substantially by proteins in their ground or their excited states to raise said nucleic acids to energy states higher than said excited acids state to thereby cause photolysis of said nucleic acids while minimizing the photolysis of said proteins. Illustrative conditions for this embodiment are as follows: said excited state comprises nucleic acid in its singlet or triplet state and said second pulse is applied during the singlet or triplet lifetime of said portion of said nucleic acids; said second light pulse is applied within 1 picosecond after said first light pulse or said first and second pulses are simultaneously applied; the wavelength of said first pulse is between 220 and 280 nanometers; the duration of said first pulse is less than $2 \times 10^{-8}$ seconds, preferably a duration between about $1 \times 10^{-12}$ and $9 \times 10^{-10}$ seconds; said first pulse has a flux of less than about $5 \times 10^{14}$ photons per square centimeter, preferably a flux of from about $1 \times 10^{13}$ to $5 \times 10^{14}$ photons per square centimeter and more preferably a flux of about $1 \times 10^{14}$ to $5 \times 10^{14}$ photons per square centimeter; said second pulse has a wavelength above about 350 namometers, preferably a wavelength of between about 350 to 410 nanometers or between about 500 to 560 nanometers; said second pulse has a duration of less than $2 \times 10^{-8}$ seconds, preferably a duration between about $9 \times 10^{-10}$ to $1 \times 10^{-12}$ seconds; said second pulse has a flux of about $1 \times 10^{15}$ to $1 \times 10^{18}$ photons per square centimeter, preferably a flux of about $1 \times 10^{17}$ photons per square centimeter; said light pulses are pulses of laser light; said light pulses are applied by a single laser; said solution is located as a thin layer in a target region; said layer having a thickness of less than about 0.5 mm, preferably a thickness of about 0.2 mm; said solution is flowed across each millimeter of target region width at a rate of about 5 milliliters per second; said solution is a blood fraction comprising plasma proteins; said blood fraction further comprises blood cells; and said pulses are applied from a plurality of directions to strike substantially all of the plasma and serum disposed around said blood cells.

It can be seen, therefore, that unique sterilization and protein production processes are provided by present invention. These processes use pulses of intense laser light to selectively photolyze DNA in the presence of proteins, e.g., tryptophan-containing proteins. In certain embodiments, this selectivity is achieved by the use of a sequence of pulses whose wavelength, time duration, and time spacing are under the control of the laser operator. The properties of the secondary pulse or pulses are chosen such that only those molecules that absorbed light from an earlier pulse in the sequence are affected. For this reason the secondary pulse or pulses can be of extremely high intensity without causing unwanted reactions.

In another illustrative embodiment of the invention, the process is used to treat blood fractions, including blood plasma, blood serum or products thereof, which fractions are suspected of carrying viable or infectious nucleic acid-containing agents. The embodiment, for example, can comprise irradiating a target region of the fraction with ultrashort, multiple light pulses of different wavelengths and intensities. A first pulse (or pulses) having a wavelength(s) of between 220 to 280 nanometers is applied to achieve a flux in the blood fraction target region of slightly less than $5 \times 10^{14}$ photons per square centimeter. This first pulse or pulses excites the DNA or RNA in said fractions from their ground state to excited state(s). A second higher intensity pulse (or pulses) having a wavelength(s) above about 300 nanometers and a flux of between about $1 \times 10^{15}$ to about $1 \times 10^{18}$ photons per square centimeter is then applied within the excited state lifetime (e.g , up to about 6 microseconds) of said DNA or RNA. As a result, these nucleic acid-containing molecules are excited to an even higher energy state thorough a non-linear process, which higher energy state results in their substantial inactivation by photolysis.

In further illustrative particular embodiments, the sterilization processes of the present invention can be practiced by using first and second single light pulses which are either simultaneously applied or which are applied, for example, within one triplet state lifetime (approximately one microsecond) of each other. As seen from the above specific example of FIG. 2, the first light pulse can be of a wavelength absorbed by nucleic acids and raises a portion of the nucleic acids from their ground state to their triplet state. The second light pulse can be of a higher intensity and longer wavelength which is preferentially absorbed by the nucleic acids in their triplet states and raises those nucleic acids to higher energy states to thereby increase the probability that spontaneous photolysis of such nucleic acids will occur. These first and second light pulses are selected such that the photolysis of the amino acids of the proteins is proteins present in the sample. In accordance with this embodiment, the first pulse is less than $2\times10^{-8}$ seconds in duration, preferably about $10^{-10}$ to $10^{-12}$ seconds, and has a flux of $1\times10^{13}$ to $1\times10^{16}$, preferably less than $5\times10^{14}$, photons per cm$^2$. Although lower first pulse fluxes will lessen the effect of the subject radiation upon the proteins, a corresponding diminution in the number of excited DNA or RNA molecules will also result. Accordingly, the first pulse flux is preferred to be in the range of $1\times10^{13}$ to $5\times10^{14}$ photons per cm$^2$, more preferably $1\times10^{14}$ to $5\times10^{14}$ photons per cm$^2$. The second pulse preferably has a wavelength above about 350 nm, and is preferably within wavelength ranges of either 350 to 410 nm or 500 to 560 nm. It is preferred that the second pulse have a duration of less than $2\times10^{-8}$ seconds, preferably about $10^{-10}$ to about $10^{-12}$ seconds. In order to increase the probability of photolysis of the excited DNA triplets, each second pulse has a higher intensity than the first pulse, having a flux of about $1\times10^{15}$ to $1\times10^{18}$, preferably about $1\times10^{17}$ photons per cm$^2$.

For purposes of simplicity the above discussion has illustratively referred in some instances to the administration of single first and second pulses and to the intermediate state as the triplet state. In other embodiments, the process can be efficiently operated by applying a repetition of pulses having the same wavelength or a repetition of an alternating series of first and second pulses (e.g., of different wavelength) to the subject sample as it flows through a target area. Also, other excited states (e.g., the first excited singlet) can also be utilized as intermediates.

In accordance with such an embodiment, a target region of a thin layer of a blood fraction or other biological medium to be sterilized is irradiated with more than one (i.e., a repetition) of first light pulses comprising a wavelength or wavelengths within a first range of 220 to 280 nm. Each of the first light pulses has a duration of less than $2\times10^{-8}$ seconds, and together these first light pulses have a combined flux within the stated wavelength range of between about $1\times10^{13}$ to $1\times10^{16}$ photons per cm$^2$. In accordance with this embodiment, second higher intensity light pulses are repetitively applied simultaneously or up to no more than 1 microsecond, preferably one picosecond, after each of said first light pulses. These second higher intensity light pulses each have a wavelength or wavelengths within a second wavelength range above about 350 nm, each have durations of less than $2\times10^{-8}$ seconds, and together have a combined flux within the stated wavelength range of between about $1\times10^{15}$ to $1\times10^{18}$ photons per cm$^2$. Once again, the preferred second wavelength ranges are between 350 to 410 nm or 500 to 560 nm. In accordance with this embodiment, said first light pulses should be applied at a frequency of between 10 and 1,000,000 pulses per second. When this embodiment of the process, as well as others, is applied to a biological fluid that is flowed as a thin layer through a target region of a laser, the frequency of the laser pulses and the selected flow rate of the fluid to be sterilized should preferably be selected such that the fluid to be treated is exposed to the aforementioned combined fluxes prior to leaving the target region.

In the embodiment where pulses of the same wavelength are utilized, the wavelength is preferably within the range of 180 to 295 nm, more preferably 220 to 290 nm, and most preferably 220 to 280 nm. The duration of each pulse is preferably less than $1\times10^{-5}$ seconds, more preferably less than $1\times10^{-8}$ seconds, more preferably in the range of $5\times10^{-9}$ to $1\times10^{-12}$ seconds, and most preferably in the range of $1\times10^{-10}$ to $1\times10^{-12}$ seconds. When a duration of from $1\times10^{-5}$ to $1\times10^{-10}$ seconds is utilized, it is believed that the triplet state comprises the intermediate pathway. When a duration of from $1\times10^{-10}$ to $1\times10^{-14}$ seconds is utilized, it is believed that the singlet state comprises the intermediate pathway. It is preferred when utilizing pulses of the same wavelength to select conditions which favor the singlet state pathway, i.e., pulses having a duration within the above-stated range. Also, in this embodiment where pulses of the same wavelength are utilized, the pulses preferably each have a flux greater than $1\times10^{15}$, more preferably from about $1\times10^{15}$ to about $1\times10^{18}$, more preferably about $1\times10^{17}$ to about $1\times10^{18}$, and most preferably about $1\times10^{17}$, photons per square centimeter. The combined flux of the pulses is preferably about one order of magnitude higher than the flux of each pulse, i.e., it is preferred that about 10 repetitions of each pulse per unit volume of the media be utilized.

When pulses of different wavelength are utilized, the duration of the first pulses is preferably as stated immediately above. The first pulses preferably have a wavelength within the range of 180 to 350 nm, more preferably 180 to 295 nm, more preferably 220 to 290 nm, and most preferably 220 to 280 nm. The first pulses preferably each have a flux of less than $1\times10^{18}$, more preferably less than $5\times10^{14}$, more preferably $1\times10^{13}$ to $5\times10^{14}$, and most preferably $1\times10^{14}$ to $5\times10^{14}$, photons per square centimeter. The combined flux of the first pulses is preferably from $1\times10^{13}$ to $1\times10^{18}$, more preferably $1\times10^{13}$ to $1\times10^{16}$, and most preferably from $1\times10^{14}$ to $5\times10^{14}$, photons per square centimeter. The second pulses preferably each have a flux greater than $1\times10^{15}$, more preferably from $1\times10^{15}$ to $1\times10^{18}$, and most preferably about $1\times10^{17}$, photons per square centimeter. The combined flux of the pulses is, for the reason stated above, about one order of magnitude higher than the flux of each pulse. The preferred wavelength for the second pulses depends upon the duration selected for the first pulses.

Thus, when a duration for the first pulses favoring the triplet state pathway is utilized ($1\times10^{-5}$ to $1\times10^{-10}$ seconds), the second pulses preferably each have a wavelength greater than 300 nm, preferably in the range of 300 to 700 nm, more preferably 300 to 450 nm, and most preferably 350 to 410 nm. In this embodiment, it is preferred that the duration of each second pulse is less than $1\times10^{-5}$, more preferably less than $1\times10^{-6}$, more preferably less than $1\times10^{-8}$ seconds, preferably in the range of $5\times10^{-9}$ to $1\times10^{-12}$ seconds and more preferably in the range of $1\times10^{-10}$ to $1\times10^{-12}$ seconds. Each second pulse is preferably applied within $1\times10^{-6}$ seconds of each first pulse, and more preferably is applied substantially simultaneously with each first pulse.

When a duration for the first pulses favoring the singlet state pathway is utilized ($1\times10^{-10}$ to $1\times10^{-14}$ seconds), the second pulses preferably each have a wavelength greater than 300 nm, preferably in the range of 300 to 700 nm, more preferably 500 to 560 nm, and most preferably about 520 to 540 nm. In this embodiment, the duration of each second pulse preferably is in the range of $1\times10^{-10}$ to $1\times10^{-12}$ seconds, more preferably less than $3\times10^{-11}$ seconds, more preferably less than about $3\times10^{-12}$ seconds, and most preferably is in the range of $1\times10^{-11}$ to $1\times10^{-12}$ seconds. Each second pulse is preferably applied within $3\times10^{-12}$ seconds of the first pulse, more preferably is applied substantially simultaneously with the first pulse, and most preferably is applied at a time delay with respect to the first pulse of about $1\times10^{-12}$ seconds.

It will be apparaent, therefore, that in some of its broader aspects the present invention can be described as a process for treating a biological fluid containing nucleic acids and proteins, which comprises irradiating said fluid with a plurality of light pulses of wavelength and intensity selected so that said nucleic acids are photolyzed in preference to said proteins. As noted above, in certain embodiments, these pulses can be laser pulses of the same wavelength, or can comprise first and second laser pulses which have different wavelengths respectively. When pulses of the same wavelength are selected, preferred conditions are as follows: each of said pulses has a substantially the same wavelength within the range of 180 to 295 nm, preferably 220 to 290 nm, more preferably 220 to 280 nm, a duration less than $1\times10^{-5}$ seconds, preferably a duration in the range from $5\times10^{-9}$ to $1\times10^{-12}$ seconds, more preferably from $1\times10^{-10}$ to $1\times10^{-12}$ seconds, and a flux greater than $1\times10^{15}$, preferably in the range from $1\times10^{15}$ to $1\times10^{18}$, more preferably $1\times10^{17}$ to $1\times10^{18}$, photons per square centimeter. When pulses of different wavelength are selected, preferred conditions are as follows: each of said first pulses has a wavelength within the range of 180 to 350 nm, a duration of less than $1\times10^{-5}$ seconds, and a flux less than $1\times10^{18}$ photons per square centimeter, and each of said second pulses has a wavelength within the range of 300 to 700 nm, a duration of less than $1\times10^{-5}$ seconds and a flux of greater than $1\times10^{15}$ photons per square centimeter. Further preferred conditions when pulses of different wavelengths are selected are as follows: each of said first pulses has a wavelength within the range of 180 to 295 nm, a duration of from $1\times10^{-10}$ to $1\times10^{-14}$ seconds, and a flux of $1\times10^{13}$ to $5\times10^{14}$ photons per square centimeter, and each of said second pulses has a wavelength within the range of 500 to 560 nm, a duration in the range of $1\times10^{-10}$ to $1\times10^{-12}$ seconds, a flux of $1\times10^{15}$ to $1\times10^{18}$ photons per square centimeter, and each second pulse is applied within $3\times10^{-12}$ seconds of each first pulse. Alternative preferred conditions when pulses of different wavelength are selected are as follows: each of said first pulses has a wavelength within the range of 180 to 295 nm, a duration of from $1\times10^{-5}$ to $1\times10^{-10}$ seconds, and a flux of $1\times10^{13}$ to $5\times10^{14}$ photons per square centimeter, and each second pulse has a wavelength within the range of 300 to 450 nm, a duration in the range of from $5\times10^{-9}$ to $1\times10^{-12}$ seconds, a flux of $1\times10^{15}$ to $1\times10^{18}$ photons per square centimeter, and each second pulse is applied within $1\times10^{-6}$ seconds of each first pulse.

Further embodiments of the present invention relate to methods of preparing killed virus vaccine, and to vaccines so prepared. These include the irradiation of a virus which is comprised of a nucleic acid portion and a tryptophan-containing protein coat. The subject irradiation is performed using ultra short high intensity laser pulses of different wavelengths to cause the nonlinear photolysis of the nucleic acid components of the virus while leaving their surrounding protein coats substantially intact. More specifically, these embodiments involve a process of preparing a killed virus vaccine, comprising the steps of: (a) providing a virus containing solution, said virus comprising a nucleic acid portion and a tryptophan-containing protein coat; (b) irradiating a target region of a thin layer of said virus containing solution with one or more first light pulse(s) of wavelength(s) within a first wavelength range of 220 to 280 nanometers, said first pulses each having a duration of less than $2\times10^{-8}$ seconds per pulse, and having a combined flux within said first wavelength range of between about $1\times10^{13}$ to $1\times10^{16}$ photons per square centimeter; and (c) irradiating said target region of said layer with one or more second higher intensity light pulse(s) of wavelengths(s) within a second wavelength range above about 350 nanometers, said second pulses each having a duration of less than $2\times10^{-8}$ seconds, and each having a flux within said second wavelength range of at least about $1\times10^{15}$ photons per square centimeter, each of said second pulse(s) being applied to said layer within up to one microsecond after each of said first pulse(s), whereby said nucleic acid portion of said virus is inactivated while alteration of the structure of said protein coat is minimized. Preferred conditions for this embodiment are as follows: said combined flux within said first wavelength range is between about $1\times10^{14}$ and $5\times10^{14}$ photons per square centimeter; each of said second pulses within said second wavelength range has a flux of about $1\times10^{17}$ to $1\times10^{18}$ photons per square centimeter; said first pulses and said second pulses each have a duration of between about $9\times10^{-10}$ and $1\times10^{-12}$ seconds; said second wavelength range is 360 to 410 nanometers or 500 to 560 nanometers; said first pulses are applied at a frequency of between 10 and 1,000,000 pulses per second; said first and second pulses are applied substantially simultaneously; said layer has a thickness of less than 0.5 mm; said layer has a thickness of about 0.2 mm; said fraction is flowed through said target region at a rate which exposes each portion thereof to said combined fluxes, e.g., flowed across each millimeter of target region width at a rate of about 5 ml per second; and said light pulses are laser pulses.

Further preferred embodiments of the present invention relate to processes for producting tryptophan-containing proteins, and to proteins so produced. They comprise culturing cells of mammalian origin to produce those proteins, causing or permitting those cells to release those proteins into a harvest medium and inactivating nucleic acid components in that medium by exposing that medium to a plurality of pulses of high intensity laser light of different wavelengths which are differentially absorbed by those nucleic acid components in their ground and excited states. Using this process, nucleic acid inactive, protein rich end products are produced. More specifically, this embodiment can involve a process for producing tryptophan-containing proteins, comprising the steps of: (a) providing cells of mammalian origin which, when cultured, produce said tryptophan-containing proteins; (b) culturing said cells; (c) releasing said proteins into a medium; and (d) inactivating the nucleic acid components in said medium by exposing said medium by exposing said medium to a plurality of pulses of high intensity laser light of different wavelengths which are differentially absorbed by said nucleic acid components in their ground and excited states to produce nucleic acid inactive, protein rich end products. Preferably, said inactivating step further comprises irradiating said medium with a first light pulse of a first wavelength of sufficient flux to raise a portion of said nucleic acid components from their ground state to an excited state, yet not sufficient to inactivate the proteins in said solution. More preferably, said inactivating step further comprises irradiating said nucleic acids while in said excited state with a second light pulse which is absorbed by nucleic acids in said excited state, but not substantially by said proteins in their ground state, to raise said acids to higher energy states to thereby cause photolysis of said nucleic acids while minimizing the photolysis of said proteins. Preferred conditions for this embodiment are as follows: said second pulse is applied during the triplet lifetime of said portion of said nucleic acids, or said second light pulse is applied within 1 picosecond after said first light pulse, or said first and second pulses are simultaneoulsy applied; the wavelength of said first pulse is between 220 and 280 nanometers; the duration of said first pulse and said second pulse is less than $2 \times 10^{-8}$ seconds, preferably the duration of said first pulse and said second pulse is between about $1 \times 10^{-12}$ and $9 \times 10^{-10}$ seconds; said first pulse has a flux of less than about $5 \times 10^{14}$ photons per square centimeter, preferably a flux of between about $1 \times 10^{13}$ and $5 \times 10^{14}$ photons per square centimeter and more preferably a flux of about $1 \times 10^{14}$ to $5 \times 10^{14}$ photons per square centimeter; said second pulse has a wavelength above about 350 nanometers, preferably a wavelength of between about 350 to 410 nanometers or between about 500 to 560 nanometers; said second pulse has a flux of about $1 \times 10^{15}$ to $1 \times 10^{18}$ photons per square centimeter; preferably a flux of about $1 \times 10^{17}$ photons per square centimeter; said light pulses are pulses of laser light; and said light pulses are applied by a single laser.

As noted, the process of the present invention is preferably applicable to such biological fluids as blood sera or blood fractions; media of mammalian cell origin containing proteinaceous products and a nucleic acid component; and viruses having tryptophan-containing protein coats. Those of ordinary skill in the art will recognize, however, that each of these embodiments will prefer a different degree of nucleic acid inactivation and will tolerate a different degree of protein analysis. Since killed virus vaccines may have some live virus, and need not retain all of the original protein coat intact, it is anticipated that reductions in nucleic acid or Viral activity in this application can be as low as $10^4$, preferably $10^6$, and photolysis of viral protein coats as high as about 40%, preferably 20%. By contrast, in blood and mammalian cell product applications, nucleic acid or viral activity reductions of at least $10^6$, preferably $10^8$, are sometimes desired. In blood or in applications involving the production of pharmaceutical products (such as insulin or other physiologic proteins), protein inactivation should not exceed 35%, preferably 20%, more preferably 5%, and most preferably less than 2%. Where the proteinaceous products are intended for non-pharmaceutical uses, lower protein yields can be accepted in order to optimize other process parameters.

Additional embodiments of the invention are illustrated in the following examples which are understood to be simulated and prophetical rather than as representations of work actually done.

EXAMPLE 1

This example illustrates the application of an embodiment of the present invention to sterilize a biological media comprising human plasma. The protein activity of the plasma can be assayed by a standard method such as the Partial Thromboplastin Time (PTT), a measure of the ability of the plasma proteins to form a clot. An increase of 3 seconds in the PTT corresponds to approximately a 10% decrease in the activity of the plasma proteins. The plasma, for purposes of this example, is deliberately infected with a mammalian virus, Simian Virus 40 (SV 40), an easily titered virus of approximately the same size as hepatitis A. A sample of the plasma is flowed through a quartz tube 0.5 mm square. The rate of flow is controlled by a pump at a rate of $3 \times 10^{-4}$ ml/sec thus establishing a flow velocity of $1.2 \times 10^{-1}$ cm/sec through the target region A Q-switched Nd:YAG laser is operated at a repetition rate of 20Hz and produces pulses of $5 \times 10^{-9}$ seconds duration. The technique of harmonic generation is used to produce two pulses from the original pulse: a first pulse of a wavelength of 266 nm and a second pulse of a wavelength of 353 nm. The pulse at 266 nm is adjusted to contain $2 \times 10^{11}$ photons and the pulse at 353 nm is adjusted to contain $1.2 \times 10^{15}$ photons. The pulses are focussed by a lens to a spot size of $4 \times 10^{-3}$ square centimeters, producing a flux of $5 \times 10^{13}$ photons/cm$^2$ at 266 nm and $3 \times 10^{17}$ photons/cm$^2$ at 353. The pulses arrive at the sample substantially simultaneously. Under these conditions, the average volume element of the plasma sample has a residence time in the target region of 0.5 seconds and therefore receives 10 repetitions of each pulse. The combined flux at 266 nm experienced by the average volume element is $5 \times 10^{14}$ photons/cm$^2$. After the sample has been processed as described, it is assayed for both viral activity and protein activity. It is found that the viral activity, as measured by the titer of SV40, has been reduced by a factor of $10^6$ and the protein activity has remained at 90% of its original value.

EXAMPLE 2

This example illustrates the application of an embodiment of the present invention in which pulses of the same wavelength are used to sterilize a biological media comprising human plasma. The plasma, for purposes of this example, is deliberately infected with bacteriophage T4 which can be titered by a plaque-forming assay on an *E. Coli.* host. The protein activity is measured by the PTT (see example 1). A sample of the plasma is flowed through a quartz tube with a cross-section 2 cm $\times$ 0.05 cm. The laser beam enters through the 2 cm face to result in an optical path length of 0.05 cm. A pump controls the flow rate of 1 ml/second, establishing a flow velocity of 10 cm/second through the target region. An excimer laser is operated to produce pulses at 258 nm with a repetition rate of 200 Hz. Each pulse has a duration of $10^{-8}$ seconds and contains $10^{17}$ photons. These pulses are passed through a cylindrical lens and onto the target region, illuminating a target area of 2 cm $\times$ 0.5 cm. At the flow rate of 1 ml/second the average volume element requires 0.05 second to traverse the target region and receives 10 laser pulses. The flux from each pulse is $10^{17}$ photons/cm$^2$ and the total flux experienced by each volume element is $10^{18}$ photons/cm$^2$. Under these conditions, the nucleic activity of the plasma sample, as assayed by the T4 titer, is reduced by a factor of $10^6$ while the protein activity has remained at 65% of its original value.

EXAMPLE 3

Example 2 is repeated except that the excimer laser is modified to produce pulses of $5 \times 10^{-12}$ seconds duration with $5 \times 10^{15}$ photons in a pulse at 258 nm. The repetition rate remains 200 Hz. The sample of the T4 in human plasma is flowed through a quartz tube of cross-section 0.5×0.05 cm and a pump regulates the flow at 0.5 ml/sec, establishing a flow velocity of 20 cm/second through the target region. The laser pulses are passed through a cylindrical lens to achieve a target region of 0.1 cm×0.5 cm. At the flow rate of 0.5 ml/sec the average volume element spends $5\times10^{-3}$ seconds in the target region and receives only one pulse from the laser. The flux of this pulse is $10^{17}$ photons/cm$^2$. Under these conditions the nucleic acid activity of the plasma sample is reduced by a factor of $10^6$ from its original value while at least 90% of the original protein activity is preserved.

EXAMPLE 4

This example illustrates the application of an embodiment of the present invention to sterilize human blood fraction Factor VIII. The activity of Factor VIII can be accurately measured by colorimetric methods commercially available in kit form. A sample of lyophilized Factor VIII is reconstituted according to the packaged instructions and, for the purpose of this example, is deliberately infected with bacteriophage T7. The titer of T7 is obtained by a plaque-forming assay on an *E. Coli.* host. The sample is flowed through a quartz tube of cross-section 0.1×0.05 cm. The laser pulses strike the 0.1 cm face and thus the optical path length is 0.05 cm. A pump establishes the flow rate at $2\times10^{-3}$ ml/sec. A passively mode-locked Nd:YAG laser operates at a repetition rate of 20 Hz. The pulses have a time duration of $20\times10^{-12}$ sec and pulses at 532 nm and 266 nm are produced by harmonic generation. The pulse at 532 nm is adjusted to contain $5\times10^{15}$ photons and the pulse at 266 nm is adjusted to contain $10^{11}$ photons. By an arrangement of mirrors and lenses the pulses are made to arrive at the target region with the peak of the 266 nm pulse $1\times10^{-12}$ seconds before the peak of the 532 nm pulse. Both pulses illuminate a cross-sectional area of $5\times10^{-3}$ cm$^2$. The average volume element of the sample is struck by 5 repetitions of each pulse, i.e., the 266 nm pulse and the 532 nm pulse. The flux of each 266 nm pulse is $2\times10^{13}$ photons/cm$^2$ and the flux of each 532 nm pulse is photons/cm$^2$. The average volume element in the sample receives a combined flux of $10^{14}$ photons/cm$^2$ at 266 nm. The sample is analyzed after treatment and it is found that the nucleic acid activity, as measured by the titer of T7, is reduced by a factor of $10^6$ while the protein activity remains at 98% of its value before irradiation.

EXAMPLES 5-11

Example 4 is repeated with all sample parameters (i.e., flow rate, target area, quartz tube cross-section) unchanged except the Nd:YAG laser is now used to run a system of dye lasers producing output pulses that are variable in wavelength. Each time the Nd:YAG laser fires, two dye laser pulses having duration $5\times10^{-12}$ seconds each are simultaneously produced. The results of the treatment in this series of examples are presented in tabular form.

| EXAMPLE | Wavelength of First Pulse (Flux = $2\times10^{13}$ photons/cm$^2$ per pulse) | Wavelength of Second Pulse (Flux = $2\times10^{18}$ photons/cm$^2$ per pulse) |
| --- | --- | --- |
| 5 | 260 | 530 |
| 6 | 270 | 530 |
| 7 | 290 | 530 |
| 8 | 240 | 530 |
| 9 | 260 | 400 |
| 10 | 260 | 600 |
| 11 | 260 | 700 |

| EXAMPLE | Fraction of Original Titer of T7 | Percent of Original Protein Activity |
| --- | --- | --- |
| 5 | $5\times10^{-7}$ | 98% |
| 6 | $10^{-6}$ | 96% |
| 7 | $10^{-1}$ | 98% |
| 8 | $10^{-3}$ | 99% |
| 9 | $10^{-5}$ | 98% |
| 10 | $10^{-4}$ | 98% |
| 11 | $10^{-3}$ | 98% |

EXAMPLE 12

This example illustrates an embodiment of the invention in the treatment of a biological media comprising human whole blood. The blood is, for purposes of this example, deliberately infected with bacteriophage T4 and the activity of the clotting proteins is measured using the PTT. The oxygen affinity of the hemoglobin proteins is monitored by standard methods. A laser system is used to produce pulses of $1\times10^{-13}$ seconds duration. Each pulse has a flux of $5\times10^{15}$ photons at a wavelength of 260 nm. The repetition rate is 200 Hz. The sample of T4 in human plasma is flowed through a quartz tube of cross-section 0.5×0.5 cm and a pump regulates the flow at 0.5 ml/cm, establishing a flow velocity of 20 cm/second through the target region. The laser pulses are passed through a cylindrical lens to achieve a target region of 0.1 cm×0.5 cm. The flux of each pulse at the target region is thus $1\times10^{17}$ photons/cm$^2$. Pulses of this duration and intensity are found to effectively penetrate ("bleach") red blood cells. Results indicate that nucleic acid activity, as measured by the titer of T4, is reduced by a factor of $10^6$ while 90% of the original clotting protein activity is maintained and the oxygen affinity of the hemoglobin proteins shows no observable decrease.

In sum, the present invention provides a generic process for sterilization of biological media with a wide variety of specific embodiments. In these embodiments, pulses of light, preferably intense laser light, are used to selectively photolyze DNA- or RNA-containing nucleic acids in the presence of proteins. This selectively is achieved by the use of a pulses whose wavelength, time duration, time spacing, and intensity, are under the control of the laser operator, following the teachings herein.

From the above, those ordinary skill in this art will recognize the applicability of this process to selectively photolyze the nucleic acid components in preference to and in the presence of proteins. Those of ordinary skill in this art will further recognize that conventional laser crystals, electronics and optics can be used to readily practice the described process of the present invention. Those of ordinary skill in the art will also recognize that the exact laser power, wavelength, optimum sample handling, and so on may be varied somewhat in view of the foregoing description to achieve optimum results without departing from the scope of the present invention, which is described more particularly in the appended claims.

We claim:

1. Process for treating a biological medium to photolyze nucleic acids in preference to proteins present therein, which comprises irradiating said medium with pulsed light of wavelength and flux selected so that (1) the nucleic acids in their ground state absorb radiation and thereby rise to an excited state or states, (2) the nucleic acids in their excited states absorb radiation and thereby rise to higher energy states and undergo photolysis to the extent that nucleic acid activity is reduced by at least 90%, and (3) the proteins in their ground or their excited states do not absorb sufficient radiation to undergo substantial photolysis.

2. Process of claim 1 wherein the biological medium is a solution selected from blood, blood fractions, genetically engineered proteinaceous products of mammalian cells, and vaccine preparations containing viral DNA or RNA in a protein coat.

3. Process of claim 2 wherein the photolysis reduces nucleic acid activity by at least a factor of $10^4$ and reduces protein functionality by no more than 40%.

4. Process of claim 3 wherein the biological medium is selected from whole blood, blood plasma, blood serum, blood factor VIII, and blood factor XI; said medium comprises nucleic acids in the form of DNA- or RNA-containing pathogens; and the photolysis reduces nucleic acid activity by at least a factor of $10^6$ and reduces protein functionality by no more than 35%.

5. Process of claim 3 wherein the biological medium is a genetically engineered proteinaceous product of mammalian cells; said medium comprises nucleic acids in the form of active mamalian DNA or RNA; and the photolysis reduces nucleic acid activity by at least a factor of $10^6$ and reduces protein functionality by no more than 35%.

6. Process of claim 3 wherein the biological medium is a vaccine preparation, said medium comprises nucleic acids in the form of viral DNA or RNA in a protein coat; and the photolysis reduces nucleic acid and thus viral activity by at least a factor of $10^4$ and reduces functionality of the protein coat by no more than 40%.

7. Process of claims 4, 5 or 6 wherein the biological medium is an aqueous solution comprising tryptophan-containing proteins; the photolysis reduces substantially all of the nucleic acid activity, and reduces substantially none of the protein functionality.

8. Process of claim 1 wherein the pulsed light is comprised of laser pulses having substantially the same wavelength.

9. Process of claim 8 wherein each of said pulses has a wavelength within the range of 180 to 295 nm, a duration less than $1 \times 10^{-5}$ seconds and a flux greater than $1 \times 10^{15}$ photons per square centimeter.

10. Process of claim 9 wherein said wavelength is 220 to 290 nm, said duration is in the range of from $5 \times 10^{-9}$ to $1 \times 10^{-15}$ seconds, and said flux is in the range of from $1 \times 10^5$ to $1 \times 10^{18}$ photons per square centimeter.

11. Process of claim 9 wherein said wavelength is 220 to 280 nm, said duration is in the range of from $1 \times 10^{-10}$ to $1 \times 10^{-12}$ seconds, and said flux is in the range of from $1 \times 10^{17}$ to $1 \times 10^{18}$ photons per square centimeter.

12. Process of claim 1 wherein the pulsed light is comprised of laser pulses having different wavelengths.

13. Process of claim 12 wherein said laser pulses comprise one or more first pulse(s) of wavelength and flux selected so that said nucleic acids in their ground state absorb radiation and thereby rise to an excited state or states, one or more additional pulse(s) of wavelength and flux selected so that said nucleic acids in their excited states absorb radiation and thereby undergo photolysis, and said proteins do not absorb sufficient radiation from any of the pulses to undergo substantial photolysis.

14. Process of claim 13, wherein said excited states of nucleic acids are selected from the singlet state and the triplet state and wherein said additional pulse or pulses are applied during the lifetime of said excited states of nucleic acids 15. Process of claim 13 wherein said additional pulse or pulses comprise a second pulse or pulses.

16. Process of claim 15 wherein said first and second pulses are simultaneously applied.

17. Process of claim 16 wherein each of said second pulses is applied within 1 microsecond after each of said first pulses.

18. Process of claim 15 wherein said first and second pulses are applied in alternating sequences of more than one pulse each.

19. Process of claim 15 wherein said first and second pulses are applied in alternating sequences of one pulse each.

20. Process of claim 13 wherein each of said first pulses has a wavelength within the range of 180 to 350 nm, a duration of less than $1 \times 10^{-5}$ seconds, and a flux less than $1 \times 10^{18}$ photons per square centimeter, and each of said second pulses has a wavelength within the range of 300 to 700 nm, a duration of less than $1 \times 10^{-5}$ seconds and a flux of greater than $1 \times 10^{15}$ photons per square centimeter.

21. Process of claim 20 wherein each of said first pulses has a wavelength within the range of 180 to 295 nm, a duration of from $1 \times 10^{-10}$ to $1 \times 10^{-14}$ seconds, and a flux of $1 \times 10^{13}$ to $5 \times 10^{14}$ photons per square centimeter, and each of said second pulses has a wavelength within the range of 500 to 560 nm, a duration in the range of $1 \times 10^{-10}$ to $1 \times 10^{-12}$ seconds, a flux of $1 \times 10^{15}$ to $1 \times 10^{18}$ photons per square centimeter, and each second pulse is applied within $3 \times 10^{-12}$ seconds of each first pulse.

22. Process of claim 20 wherein each of said first pulses has a wavelength within the range of 180 to 295 nm, a duration of from $1 \times 10^{-5}$ to $1 \times 10^{-10}$ seconds, and a flux of $1 \times 10^{13}$ to $5 \times 10^{14}$ photons per square centimeter, and each second pulse has a wavelength within the range of 300 to 450 nm, a duration in the range of from $5 \times 10^{-9}$ to $1 \times 10^{-12}$ seconds, a flux of $1 \times 10^{15}$ to $1 \times 10^{18}$ photons per square centimeter, and each second pulse is applied within $1 \times 10^{-6}$ seconds of each first pulse.

23. Process for treating a biological fluid containing nucleic acids and proteins, which comprises irradiating said fluid with a plurality of laser pulses of wavelength and intensity selected so that said nucleic acids are photolyzed in preference to said proteins.

24. Process of claim 23, wherein said laser pulses comprise a first pulse of a first wavelength and flux sufficient to raise a substantial portion of said nucleic acids from their ground state to an excited state, yet not sufficient to photolyze a substantial portion of said proteins.

25. Process of claim 24, wherein said laser pulses further comprise a second pulse which is preferentially absorbed by the nucleic acids in said excited state, but not substantially by said proteins, to thereby cause photolysis of said nucleic acids while minimizing photolysis of said proteins.

26. Process of claim 23 wherein each of said pulses has substantially the same wavelength within the range of 180 to 295 nm, a duration less than $1\times 10^{-5}$ seconds and a flux greater than $1\times 10^{15}$ photons per square centimeter.

27. Process of claim 26 wherein said wavelength is 220 to 290 nm, said duration is in the range of from $5\times 10^{-9}$ to $1\times 10^{-12}$ seconds, and said flux is in the range of from $1\times 10^{15}$ to $1\times 10^{18}$ photons per square centimeter.

28. Process of claim 27 wherein said wavelength is 220 to 280 nm, said duration is in the range of from $1\times 10^{-10}$ to $1\times 10^{-12}$ seconds, and said flux is in the range of from $1\times 10^{17}$ to $1\times 10^{18}$ photons per square centimeter.

29. Process of claim 23 wherein said pulses comprise first and second pulses which have different wavelengths respectively.

30. Process of claim 29 wherein each of said first pulses has a wavelength within the range of 180 to 350 nm, a duration of less than $1\times 10^{-5}$ seconds, and a flux less than $1\times 10^{18}$ photons per square centimeter, and each of said second pulses has a wavelength within the range of 300 to 700 nm, a duration of less than $1\times 10^{-5}$ seconds and a flux of greater than $1\times 10^{15}$ photons per square centimeter.

31. Process of claim 30 wherein each of said first pulses has a wavelength within the range of 180 to 295 nm, a duration of from $1\times 10^{-10}$ to $1\times 10^{-14}$ seconds, and a flux of $1\times 10^{13}$ to $5\times 10^{14}$ photons per square centimeter, and each of said second pulses has a wavelength within the range of 500 to 560 nm, a duration in the range of $1\times 10^{-10}$ to $1\times 10^{-12}$ seconds, a flux of $1\times 10^{15}$ to $1\times 10^{18}$ photons per square centimeter, and each second pulse is applied within $3\times 10^{-12}$ seconds of each first pulse.

32. Process of claim 31 wherein each of said first pulses has a wavelength within the range of 180 to 295 nm, a duration of from $1\times 10^{-5}$ to $1\times 10^{-10}$ seconds, and a flux of $1\times 10^{13}$ to $5\times 10^{14}$ photons per square centimeter, and each second pulse has a wavelength within the range of 300 to 450 nm, a duration in the range of from $5\times 10^{-9}$ to $1\times 10^{-12}$ seconds, a flux of $1\times 10^{15}$ to $1\times 10^{18}$ photons per square centimeter, and each second pulse is applied within $1\times 10^{-6}$ seconds of each first pulse.

33. A method of treating a solution of proteins and nucleic acids to selectively inactivate said nucleic acids, comprising: (a) irradiating said solution with a first light pulse of a first wavelength of sufficient flux to raise a portion of said nucleic acids from their ground state to an excited state yet not sufficient to inactivate the proteins in said solution; and (b) irradiating said nucleic acids while in said excited state with a second light pulse which is preferentially absorbed by nucleic acids in said excited state but not substantially by proteins in their ground state, to raise said nucleic acids to energy states higher than said excited state to thereby cause photolysis of said nucleic acids while minimizing the photolysis of said proteins.

34. The method of claim 33, wherein said excited state comprises nucleic acid in its triplet state or singlet state and wherein said second pulse is applied during the triplet or singlet lifetime of said portion of said nucleic acids.

35. The method of claim 33, wherein said first and second pulses are simultaneously applied.

36. The method of claim 33 wherein said second light pulse is applied within 1 picosecond after said first light pulse.

37. The method of claim 33 wherein the wavelength of said first pulse is between 220 and 280 nanometers.

38. The method of claim 33 wherein the duration of said first pulse is less than $2\times 10^{-8}$ seconds.

39. The method of claim 33 wherein the duration of said first pulse is between about $1\times 10^{-12}$ and $9\times 10^{-10}$ seconds.

40. The method of claim 33 wherein said first pulse has a flux of less than about $5\times 10^{14}$ photons per square centimeter.

41. The method of claim 40 wherein said first pulse has a flux of between about $1\times 10^{13}$ and $5\times 10^{14}$ photons per square centimeter.

42. The method of claim 33 wherein said second pulse has a wavelength above about 350 nanometers.

43. The method of claim 42 wherein said second pulse has a wavelength of between about 350 to 410 nanometers.

44. The method of claim 43 wherein said second pulse has a wavelength of between about 500 to 560 nanometers.

45. The method of claim 33 wherein said second pulse has a duration of less than $2\times 10^{-8}$ seconds.

46. The method of claim 45 wherein said second pulse has a duration of between about $9\times 10^{-10}$ to $1\times 10^{-12}$ seconds.

47. The method of claim 33 wherein said second pulse has a flux of about $1\times 10^{15}$ to $1\times 10^{18}$ photons per square centimeter.

48. The method of claim 47 wherein said second pulse has a flux of about $1\times 10^{17}$ photons per square centimeter.

49. The method of claim 33 wherein said light pulses are pulses of laser light.

50. The method of claim 49 wherein said light pulses are applied by a single laser.

51. The method of claim 33 wherein said solution is located as a thin layer in a target region, said layer having a thickness of less than about 0.5 nm.

52. The method of claim 51 wherein said layer has a thickness of about 0.2 nm.

53. The method of claim 52 wherein said solution is flowed across each millimeter of target region width at a rate of about 5 milliliters per second.

54. The method of claim 33 wherein said solution is a blood fraction comprising plasma proteins.

55. The method of claim 54 wherein said blood fraction further comprises blood cells, and wherein said pulses are applied from a plurality of directions to strike substantially all of the plasma and serum disposed around said blood cells.

* * * * *